United States Patent [19]

Lees et al.

[11] 4,262,122
[45] Apr. 14, 1981

[54] PREPARATION OF 5,5-DIMETHYL-2-HYDRAZINO-1,4,5,6-TETRAHYDRO-PYRIMIDINE HYDROHALIDE

[75] Inventors: Robert G. Lees, Stamford, Conn.; Andrew S. Tomcufcik, Old Tappan, N.J.

[73] Assignee: American Cyanamid Company, Stamford, Conn.

[21] Appl. No.: 122,940

[22] Filed: Feb. 19, 1980

[51] Int. Cl.$^3$ ............................................. C07D 239/14
[52] U.S. Cl. ..................................................... 544/330
[58] Field of Search ......................................... 544/330

[56] References Cited

U.S. PATENT DOCUMENTS 3,931,152  1/1976  Tomcufcik et al. ............... 544/330

Primary Examiner—Paul M. Coughlan, Jr.
Attorney, Agent, or Firm—Harry H. Kline

[57] ABSTRACT

There is provided a novel process for preparing 5,5-dimethyl-2-hydrazino-1,4,5,6-tetrahydropyrimidine hydrohalide by causing neopentyldiamine to react with a guanidine hydrohalide and followed by treating the so-formed reaction product with hydrazine to yield the desired tetrahydropyrimidine hydrohalide. Alternatively, neopentyldiamine, guanidine hydrohalide and hydrazine can be admixed and reacted to yield the desired tetrahydropyrimidine hydrohalide.

6 Claims, No Drawings

PREPARATION OF 5,5-DIMETHYL-2-HYDRAZINO-1,4,5,6-TETRAHYDRO-PYRIMIDINE HYDROHALIDE

The present invention relates to the preparation of 5,5-dimethyl-2-hydrazino-1,4,5,6-tetrahydropyrimidine hydrohalide. More particularly, it relates to the preparation of 5,5-dimethyl-2-hydrazino-1,4,5,6-tetrahydropyrimidine hydrohalide in an economical manner absent environmental contamination. Still more particularly, the invention is concerned with a novel process involving the reaction of a pyrimidine amino derivative with hydrazine.

It is known that 5,5-dimethyl-2-hydrazino-1,4,5,6-tetrahydropyrimidine hydrohalide can be prepared by a plurality of steps which, unfortunately, are not entirely satisfactory. In an illustrative process, there is initially reacted 1,3-diamino-2,2-dimethyl propane with carbon disulfide to yield 5,5-dimethyl-1,4,5,6-tetrahydropyrimidine-2-thiol. The latter is next treated with bromoethane in refluxing ethanol to form 5,5-dimethyl-2-ethylthio-1,4,5,6-tetrahydropyrimidine hydrobromide. Finally, the latter is reacted with hydrazine to obtain 5,5-dimethyl-2-hydrazino-1,4,5,6-tetrahydropyrimidine hydrobromide, an intermediate useful in the preparation of substituted 1,4-pentadien-3-one substituted amidino hydrazone salts effective for the control of fire ants. It will be seen from the synthesis outlined that corrosive, inorganic sulfur compounds as well as mercaptans are produced. If a process could be developed which would avoid the above difficulties, a long felt need in the art would be met.

It is, therefore, a principal object of the invention to obtain the desired pyrimidine hydrohalide by utilizing non-corrosive, non-sulfur, reactive materials. It is a further object of the invention to utilize either a single overall reaction or at most a two-step process for attaining the desired pyrimidine compound. Other objects and advantages will become apparent from a reading of the ensuing description.

It has been unexpectedly found that 2-hydrazino-5,5-dimethyl-1,4,5,6-tetrahydropyrimidine and the salts thereof can be prepared in a straightforward manner involving either an overall one-step process or a two-step procedure. The overall process involves the reaction of neopentyldiamine (i.e., 1,3-diamino-2,2-dimethyl propane) and guanidine hydrohalide to obtain 2-amino-5,5-dimethyl-1,4,5,6-tetrahydropyrimidine hydrohalide which is next combined with at least an equivalent, or preferably a slight excess of hydrazine, to form 2-hydrazino-5,5-dimethyl-1,4,5,6-tetrahydropyrimidine and the hydrohalide salts thereof in good yield and purity absent the use of corrosive carbon disulfide reactant as well as hydrogen sulfide and alkyl mercaptan by-products.

According to the process of the invention, there is reacted at temperatures ranging from about 110° C. to about 160° C. equimolar amounts of neopentyl diamine and guanidine hydrohalide such as guanidine hydrochloride or hydrobromide and equivalents thereof, to obtain the corresponding 2-amino-5,5-dimethyl-1,4,5,6-tetrahydropyrimidine hydrohalide which is further reacted with an equivalent, or preferably more, of hydrazine to obtain 2-hydrazino-5,5-dimethyl-1,4,5,6-tetrahydropyrimidine hydrohalide in good yield and purity at least equimolar amounts of the reactants, namely, neopentyldiamine, guanidine hydrohalide, and hydrazine are employed and are within the contemplation of the present disclosure.

Although the invention is described utilizing a guanidine hydrohalide, an equivalent thereof, such as cyanogen chloride, cyanogen bromide, cyanogen iodide, melamine, cyanamide, dimethylcyanamide, or dicyandiamide can also be employed.

In general, the hydrazine reaction is carried out, preferably in an inert atmosphere at a temperature ranging from about 110° C. to about 160° C. Advantageously, the hydrazine reactant may be combined with the guanidine reactant in a one-step reaction scheme at a temperature ranging from about 120° C. to about 135° C., or higher, to attain the desired hydrazino pyrimidine derivative in good yield and purity.

The following examples are presented primarily for the purpose of illustrating certain more specific details of the invention. The latter is not to be deemed limited except as defined in the claims. Unless otherwise noted, all parts are by weight.

EXAMPLE 1

Preparation of 2-Amino-5,5-Dimethyl-1,4,5,6-Tetrahydropyrimidine Hydrochloride Neopentyldiamine (47.91 parts) and 44.79 parts of guanidine hydrochloride are combined in a suitable flask equipped with condenser and magnetic stirring bar. The flask is flushed with argon and then placed in an oil bath preheated to 140° C. Within ten minutes, a clear, homogeneous melt resulted and ammonia evolution began. The reaction mixture is stirred at 140° C.–147° C. under a stream of argon for eleven hours and then left overnight at room temperature.

The crude resultant product consists of white crystals suspended in a yellow glass. This material is taken up in ethanol and the ethanol is evaporated on the rotary evaporator. This process is repeated two times. During the last evaporation, the residue solidified. The white solid is left overnight on the vacuum pump. There is obtained 2-amino-5,5-dimethyl-1,4,5,6-tetrahydropyrimidine hydrochloride in a yield of 99.6% having a purity greater than 95%.

In lieu of guanidine hydrochloride, the corresponding hydrobromide or cyanogen chloride is employed with attendant good results.

EXAMPLE 2

Preparation of 2-Hydrazino-5,5-Dimethyl-1,4,5,6-Tetrahydropyrimidine Hydrochloride The product (2.60 parts) of Example 1 above, 2-amino-5,5-dimethyl-1,4,5,6-tetrahydropyrimidine hydrochloride, is added to a suitable flask equipped with condenser and magnetic stirring bar, and flushed with argon. There is next added 1.19 parts, 1.5 equivalents, of hydrazine hydrate, and the mixture is stirred until a clear solution is obtained. The flask is then placed in an oil bath preheated to 115° C. Ammonia is evolved almost immediately. The reaction is maintained at 115°–120° C. under a stream of argon for twelve hours. After sitting overnight at room temperature, the flask contains a white, crystalline solid and a small amount of clear, colorless liquid. The liquid is evaporated at room temperature. Resultant yield of 2-hydrazino-5,5-dimethyl-1,4,5,6-tetrahydropyrimidine hydrochloride which is found to be 97% pure is almost quantitative.

EXAMPLE 3

Preparation of 5,5-Dimethyl-2-Hydrazino-1,4,5,6-Tetrahydropyrimidine Hydrochloride Neopentyl diamine (3.14 parts), 2.94 parts of guanidine hydrochloride, and 2.32 parts of hydrazine hydrate are combined in a suitable flask equipped with condenser and magnetic stirring bar under an argon atmosphere. The mixture is stirred and warmed slightly until a clear solution is obtained. The flask is then placed in an oil bath which has been preheated to 124° C. Ammonia is evolved almost immediately. Resultant reaction mixture is maintained at 124° C. under a stream of argon for about eight hours. After sitting overnight at room temperature, the flask contains a white solid and a small amount of clear liquid. This mixture is triturated with isopropyl alcohol and filtered. The white crystalline product is washed with isopropyl alcohol and dried overnight in a vacuum desiccator.

There is recovered 2-hydrazino-5,5-dimethyl-1,4,5,6-tetrahydropyrimidine hydrochloride in 85% yield and is found to be pure by $^{13}$C-NMR analysis. No starting material or intermediate (2-amino-5,5-dimethyl tetrahydropyrimidine hydrochloride) can be detected.

We claim:

1. A process for the preparation of 5,5-dimethyl-2-hydrazino-1,4,5,6-tetrahydropyrimidine hydrohalide which comprises: reacting in at least equimolar amounts neopentyldiamine, hydrazine hydrate and guanidine hydrohalide, at a temperature ranging from about 110° C. to about 160° C., and recovering resultant 5,5-dimethyl-2-hydrazino-1,4,5,6-tetrahydropyrimidine hydrohalide in good yield and purity.

2. The process according to claim 1 wherein the guanidine hydrohalide is guanidine hydrochloride.

3. The process according to claim 1 wherein a mixture of neopentyldiamine and guanidine hydrohalide is initially reacted to form 5,5-dimethyl-2-amino-1,4,5,6-tetrahydropyrimidine hydrochloride and further reacting the latter with the hydrazine reactant.

4. The process according to claim 3 wherein the guanidine hydrohalide is guanidine hydrochloride.

5. In a process for the preparation of 5,5-dimethyl-2-hydrazino-1,4,5,6-tetrahydropyrimidine hydrohalide, the improvement which comprises: reacting a 5,5-dimethyl-2-amino-1,4,5,6-tetrahydropyrimidine hydrohalide with at least an equivalent of hydrazine hydrate at a temperature ranging from about 120° C. to about 135° C. and recovering 5,5-dimethyl-2-hydrazino-1,4,5,6-tetrahydropyrimidine hydrohalide in good yield and purity.

6. The process according to claim 5 wherein the hydrohalide is hydrochloride.

* * * * *